United States Patent
Mimura et al.

(10) Patent No.: US 9,658,237 B2
(45) Date of Patent: May 23, 2017

(54) AUTOMATIC ANALYZER

(71) Applicant: HITACHI HIGH-TECHNOLOGIES CORPORATION, Tokyo (JP)

(72) Inventors: Tomonori Mimura, Tokyo (JP); Akihisa Makino, Tokyo (JP); Manabu Ando, Tokyo (JP); Sakuichiro Adachi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 135 days.

(21) Appl. No.: 14/415,300

(22) PCT Filed: Jun. 13, 2013

(86) PCT No.: PCT/JP2013/066377
§ 371 (c)(1),
(2) Date: Jan. 16, 2015

(87) PCT Pub. No.: WO2014/013820
PCT Pub. Date: Jan. 23, 2014

(65) Prior Publication Data
US 2015/0185242 A1    Jul. 2, 2015

(30) Foreign Application Priority Data

Jul. 20, 2012 (JP) ................................ 2012-161629

(51) Int. Cl.
*G01N 35/02* (2006.01)
*G01N 21/31* (2006.01)
(Continued)

(52) U.S. Cl.
CPC ......... *G01N 35/025* (2013.01); *G01N 21/13* (2013.01); *G01N 21/272* (2013.01); *G01N 21/31* (2013.01);
(Continued)

(58) Field of Classification Search
None
See application file for complete search history.

(56) References Cited

U.S. PATENT DOCUMENTS

| 8,700,345 B2 * | 4/2014 | Okabayashi ......... G01N 35/025 250/573 |
| 2008/0158552 A1 * | 7/2008 | Tokunaga ............ G01N 21/253 356/73 |

(Continued)

FOREIGN PATENT DOCUMENTS

| EP | 2 453 224 A1 | 5/2012 |
| JP | 61-241639 A | 10/1986 |

(Continued)

OTHER PUBLICATIONS

Extended European Search Report received in corresponding European Application No. 13820255.1 dated Mar. 1, 2016.

(Continued)

*Primary Examiner* — Jill Warden
*Assistant Examiner* — Benjamin Whatley
(74) *Attorney, Agent, or Firm* — Mattingly & Malur, PC (57) ABSTRACT

There is provided an automatic analyzer including: a sample pipetting mechanism 7, reagent pipetting mechanisms 12A and 12B, mixing mechanisms 33A and 33B, a scattered light photometer 40, and an absorption photometer 41 all located on a transfer path of reaction cells 2 arranged circumferentially on a disk-shaped reaction disk 1, the reaction cells 2 being transferred in the circumferential direction by rotation of the reaction disk 1. Scattered light intensity and absorbance are controlled to be measured by causing the reaction cells 2 to move past a scattered light detection position and a transmitted light detection position in the same process of movement, the two positions being established beforehand on the transfer path. This makes it possible to suppress the effects on measurement results of the difference in time (Continued)

between scattered light measurement and absorbance measurement thereby improving measurement accuracy.

5 Claims, 8 Drawing Sheets

(51) Int. Cl.
*G01N 21/13* (2006.01)
*G01N 21/49* (2006.01)
*G01N 21/51* (2006.01)
*G01N 21/53* (2006.01)
*G01N 21/59* (2006.01)
*G01N 35/00* (2006.01)
*G01N 21/27* (2006.01)
*G01N 35/04* (2006.01)

(52) U.S. Cl.
CPC ............ *G01N 21/49* (2013.01); *G01N 21/51* (2013.01); *G01N 21/532* (2013.01); *G01N 21/59* (2013.01); *G01N 35/00613* (2013.01); *G01N 2035/0453* (2013.01); *G01N 2201/02* (2013.01); *G01N 2201/062* (2013.01)

(56) References Cited

U.S. PATENT DOCUMENTS

| | | | | |
|---|---|---|---|---|
| 2010/0178206 A1* | 7/2010 | Obata | ............... | G01N 21/51 422/73 |
| 2012/0141330 A1* | 6/2012 | Adachi | ............... | G01N 21/51 422/82.05 |
| 2013/0108509 A1 | 5/2013 | Shiba et al. | | |
| 2013/0294974 A1 | 11/2013 | Shiba et al. | | |
| 2014/0271369 A1* | 9/2014 | Fritchie | ............... | G01N 35/025 422/82.09 |

FOREIGN PATENT DOCUMENTS

| | | |
|---|---|---|
| JP | 63-205546 | 8/1988 |
| JP | 01-295134 | 11/1989 |
| JP | 6-109743 A | 4/1994 |
| JP | 10-332582 | 12/1998 |
| JP | 2007-322324 | 12/2007 |
| JP | 2008-008794 | 1/2008 |
| WO | 2008/139978 A1 | 11/2008 |
| WO | 2011/162113 A1 | 12/2011 |
| WO | 2012/077536 A1 | 6/2012 |

OTHER PUBLICATIONS

Chinese Office Action received in corresponding Chinese Application No. 20138003678.8 dated Mar. 2, 2016.
International Preliminary Report on Patentability received in International Application No. PCT/JP2013/066377 dated Jan. 29, 2015.

* cited by examiner

AUTOMATIC ANALYZER

TECHNICAL FIELD

The present invention relates to an automatic analyzer that performs qualitative and quantitative analyses of biological samples such as blood and urine.

BACKGROUND ART

Automatic analyzers analyze biological samples such as blood and urine (referred to as the sample hereunder) qualitatively and quantitatively by adding thereto reagents that react specifically to specific ingredients and by having the reactions measured with an absorption photometer and a scattered light photometer.

The techniques regarding such photometers include those disclosed in Patent Literature 1 (JP-2008-8794-A) involving an analyzer that has a transmitted light measurement system measuring the absorbance of a test liquid through which light from a light source is transmitted, and a reflected light measurement system measuring the intensity of the light emitted from the light source and reflected from the test liquid. The transmitted light measurement system is used to measure the absorbance of the test liquid until the reflected light measurement system detects the reflected light of a predetermined intensity value. Once the reflected light measurement system detects the reflected light of the predetermined intensity value, the reflected light measurement system is used thereafter to measure the intensity of the reflected light from the test liquid.

Patent Literature 2 (JP-10-332582-A) discloses techniques regarding a turbidity measurement device including: a light source that causes light to be incident on a measurement target liquid held in a light transmissive cell; an incidence-side integrating sphere that captures scattered light reflected from the cell; an exit-side integrating sphere that captures transmitted light having passed through the cell and the scattered light therefrom; an incidence-side scattered light sensor attached to a part deviating from a light transmission path of the incidence-side integrating sphere, the incidence-side scattered light sensor sensing the scattered light captured by the incidence-side integrating sphere; an exit-side transmitted light sensor attached to an extension from the light transmission path of the exit-side integrating sphere, the exit-side transmitted light sensor sensing the transmitted light captured by the exit-side integrating sphere; an exit-side scattered light sensor attached to a part deviating from the light transmission path of the incidence-side integrating sphere, the exit-side scattered light sensor sensing the scattered light captured by the exit-side integrating sphere; and turbidity calculation means that calculates turbidity based on sensing signals from the incidence-side scattered light sensor, the exit-side transmitted light sensor, and exit-side scattered light sensor.

PRIOR ART LITERATURE

Patent Literature

Patent Literature 1
JP-2008-8794-A
Patent Literature 2
JP-10(1998)-332582-A

SUMMARY OF THE INVENTION

Problem to be Solved by the Invention

The existing automatic analyzers with their above-outlined techniques analyze the sample (biological sample such as blood or urine) qualitatively and quantitatively by measuring the absorbance of, or scattered light from, the measurement target sample. In measuring absorbance, the automatic analyzer irradiates the sample with light ranging from short to long wavelengths and disperses the transmitted light therefrom. This allows the automatic analyzer to select wavelengths unaffected by bilirubin or hemoglobin, which offers the advantage of an extensive range of applications. In measuring scattered light, the automatic analyzer irradiates the sample with light of a specific wavelength and detects particle scattering in the reaction solution, which provides the advantage of high sensitivity. However, it is necessary to take into consideration the fact that the measurements are susceptible to the effects of particles in the sample. It is thus conceivable that measurement accuracy may be improved by measuring both scattered light and absorbance regarding the same measurement target sample.

However, scattered light measurement and absorbance measurement are aimed at a measurement target sample whose state varies over time after the addition of a predetermined reagent. Thus there is fear that the difference in time between scattered light measurement and absorbance measurement may affect the measurement results.

The present invention has been made in view of the above circumstances, and an object of the invention is to provide an automatic analyzer that suppresses the effects on measurement results of the difference in time between scattered light measurement and absorbance measurement thereby improving measurement accuracy.

Means for Solving the Problem

In achieving the object above, the present invention provides an automatic analyzer including: a plurality of reaction cells that hold a liquid mixture of a sample and a reagent; a disk-shaped reaction disk that has the reaction cells arranged thereon circumferentially; a sample pipetting mechanism located on a transfer path of the reaction cells transferred in the circumferential direction by rotation of the reaction disk, the sample pipetting mechanism pipetting the sample from a sample container holding the sample into the reaction cells; a reagent pipetting mechanism located on the transfer path, the reagent pipetting mechanism pipetting the reagent from a reagent container holding the reagent into the reaction cells; a mixing mechanism that mixes the liquid mixture held in the reaction cells; at least one scattered light photometer that has a scattered light detecting light source for emitting scattered light detecting light to the liquid mixture in the reaction cells moving past a scattered light detection position established beforehand on the transfer path, the scattered light photometer further having a scattered light detector for detecting scattered light emanating from the liquid mixture under the light emitted from the scattered light detecting light source, the scattered light photometer further measuring scattered light intensity from the liquid mixture; at least one absorption photometer that has a transmitted light detecting light source for emitting transmitted light detecting light to the liquid mixture in the reaction cells moving past a transmitted light detection position established beforehand on the transfer path, the absorption photometer further having a transmitted light detector for detecting transmitted light having passed through the liquid mixture under the light emitted from the transmitted light detecting light source, the absorption photometer further measuring absorbance of the liquid mixture; a control device that allows the scattered light intensity and the absorbance to be measured by causing the reaction cells to move past the scattered light detection position and the transmitted light detection position in the same process of movement; and a reaction cell washing device that washes the reaction cells.

Effect of the Invention

According to the present invention, it is possible to suppress the effects on measurement results of the difference in time between scattered light measurement and absorbance measurement thereby improving measurement accuracy.

MODE FOR CARRYING OUT THE INVENTION

One embodiment of the present invention is explained below with reference to the accompanying drawings.

Figure 1:
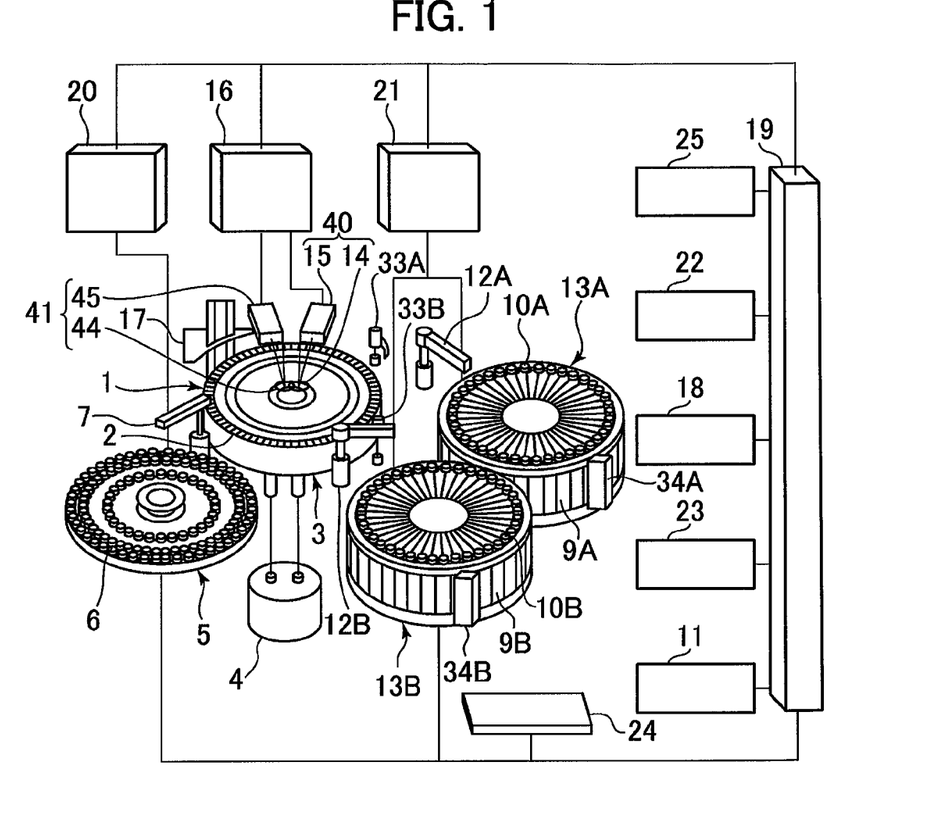
FIG. 1 is a schematic diagram showing an overall structure of an automatic analyzer as one embodiment of the present invention.
Figure 2:
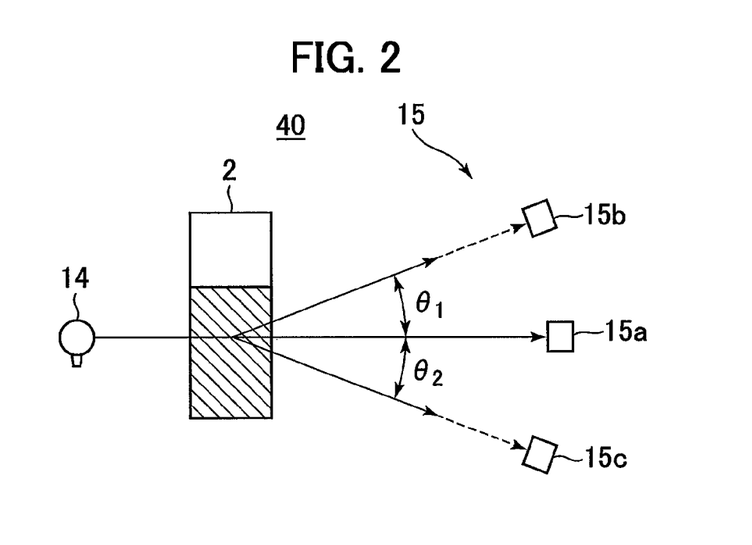
FIG. 2 is a schematic diagram showing a structure of a scattered light photometer.
Figure 3:
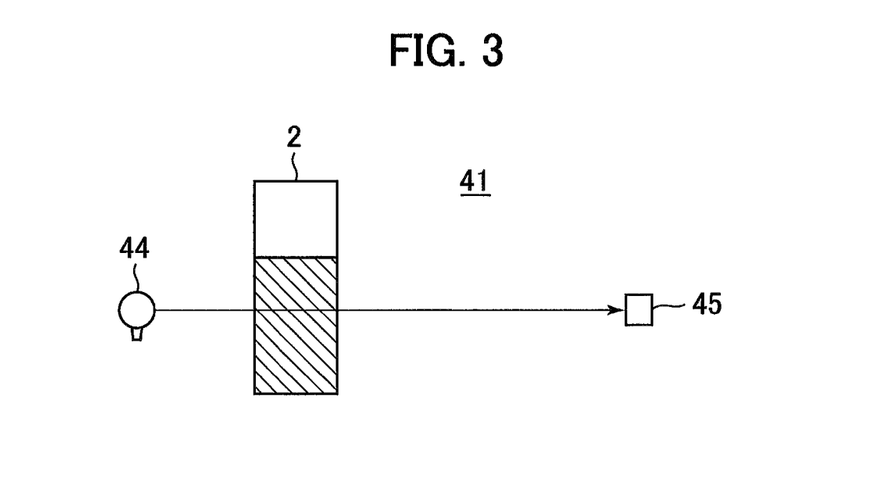
FIG. 3 is a schematic diagram showing a structure of an absorption photometer.

FIG. 1 is a schematic diagram showing an overall structure of an automatic analyzer as one embodiment of the present invention. FIGS. 2 and 3 are schematic diagrams outlining the structure of the scattered light photometer and that of the absorption photometer, respectively.

In FIG. 1, the automatic analyzer is made up of a sample disk 5, a first and a second reagent disk 13A and 13B, a reaction disk 1, a sample pipetting mechanism 7, reagent pipetting mechanisms 12A and 12B, and other functional units including a computer (control device) 18.

On the sample disk 5, a plurality of sample containers 6 holding a biological sample such as blood or urine (referred to as the sample hereunder) are arranged circumferentially. The sample disk 5 is rotatively driven by a rotation drive mechanism, not shown, to move the sample containers 6 to predetermined positions.

The first and the second reagent disks 13A and 13B are equipped with reagent cooling boxes 9A and 9B respectively. On these disks, a plurality of reagent bottles 10A and 10B are circumferentially arranged, which hold therein the reagents to be used by the automatic analyzer in handling the items of analytical processing. The first and the second reagent disks 13A and 13B are rotatively driven by rotation drive mechanisms, not shown, to move the reagent bottles 10A and 10B to predetermined positions, respectively. Further, on the first and the second reagent disks 13A and 13B, reading devices 34A and 34B are arranged, which read reagent identification information from each of the reagent bottles 10A and 10B. The reagent identification information thus read is transmitted via an interface 19 to the computer (control device) 18 along with information about the bottle positions on the first and the second reagent disks 13A and 13B. The transmitted information is associated with measurement dates and times or like data when stored into a memory (storage device) 11. For example, the reagent identification information may be represented by barcodes, and the reading devices 34A and 34B may be barcode readers.

The reaction disk 1 is furnished with a thermostatic bath (reaction vessel) 3 controlled to a predetermined temperature (e.g., 37° C.) by a constant temperature unit 4. On the reaction disk 1, a plurality of reaction vessels (reaction cells) 2 are circumferentially arranged, which hold therein a liquid mixture (also called the reaction mixture) composed of the sample and reagents. The reaction disk 1 is rotatively driven by a rotation drive mechanism, not shown, to transfer the reaction cells 2 along a transfer path in the circumferential direction. Incidentally, the rotation direction, rotation angle, and rotation speed of the reaction disk 1 are controlled by the computer (control device) 18.

The sample pipetting mechanism 7 pipettes the sample held in the sample containers 6 into the reaction cells 2 at a sample pipetting position 7a (to be discussed later with reference to FIG. 4). The reagent pipetting mechanisms 12A and 12B pipette the reagents held in the reagent bottles 10A and 10B into the reaction cells 2 at a first and a second reagent pipetting position 12a and 12b (to be discussed later with reference to FIG. 4). The liquid mixture composed of the sample and reagents, which is pipetted into the reaction cells 2 is mixed by mixing mechanisms 33A and 33B located at the pipetting positions of the reagent pipetting mechanisms 12A and 12B respectively.

The operation of the sample disk 5 and that of the sample pipetting mechanism 7 are controlled by a sample pipetting control unit 20. The operations of the first and the second reagent disks 13A and 13B, the reagent pipetting mechanisms 12A and 12B, and the mixing mechanisms 33A and 33B are controlled by a reagent pipetting control unit 21. The sample pipetting control unit 20 and the reagent pipetting control unit 21 are controlled by the computer (control device) 18 connected via the interface 18.

The reaction disk 1 is provided with at least one absorption photometer 41 and at least one scattered light photometer 40, the absorption photometer 41 detecting the absorbance of the liquid mixture (reaction mixture) composed of the sample and reagents, which is held in the reaction cells 2, the scattered light photometer 40 detecting the scattered light intensity from the reaction mixture. This embodiment is explained on the assumption that one absorption photometer 41 and one scattered light photometer 40 are provided.

As shown in FIG. 3, the absorption photometer 41 is furnished with a multi-wavelength light source (transmitted light detecting light source) 44 (such as a halogen light source) and a transmitted light detector 45, the multi-wavelength light source 44 emitting multi-wavelength light to the reaction cells 2 holding the liquid mixture (reaction mixture) composed of a measurement target sample and reagents, the transmitted light detector 45 detecting the transmitted light having passed through the reaction cells 2 and the liquid mixture (reaction mixture) held therein. The reaction cells 2 are driven circumferentially on the reaction disk 1 along the transfer path thereof. When each reaction cell 2 thus driven moves past a transmitted light detection position located between the multi-wavelength light source 44 and the transmitted light detector 45, the intensity of transmitted light is detected. The transmitted light intensity (detection result) detected by the transmitted light detector 45 is converted to digital form by an A/D converter 16, and the digitized light intensity thus converted is transmitted to the computer (control device) 18 via the interface 19.

As shown in FIG. 2, the scattered light photometer 40 is furnished with a single-wavelength light source (scattered light detecting light source) 14 (such as an LED (light emitting diode) light source) and a scattered light detector 15, the single-wavelength light source 14 emitting single-wavelength light to the reaction cells 2 holding the liquid mixture (reaction mixture) composed of the measurement target sample and reagents, the scattered light detector 15 detecting the scattered light emanating from the reaction cells 2 and the liquid mixture (reaction mixture) held therein. The scattered light detector 15 is made up of a plurality of detectors including a detector 15a positioned on the optical axis (at angle 0) of the single-wavelength light emitted from the single-wavelength light source 14, a detector 15b positioned on the circumference of a circle centering on the optical axis and positioned at angle θ1 relative to the optical axis, and a detector 15c positioned at angle θ2 relative to the optical axis. The reaction cells 2 are driven circumferentially on the reaction disk 1 along the transfer path thereof. When each reaction cell 2 thus driven moves past a scattered light detection position located between the single-wavelength light source 14 and the scattered light detector 15, the intensity of scattered light is detected. The scattered light intensity (detection result) detected by the scattered light detector 45 is converted to digital form by the A/D converter 16, and the digitized light intensity thus converted is transmitted to the computer (control device) 18 via the interface 19.

The reaction cells 22 holding the liquid mixture (reaction mixture) having been measured are each washed at a washing position by a washing mechanism 17.

Also with the automatic analyzer, a keyboard 24 as an input device, a CRT display unit 25 as a display device, a printer 22 as a print output device, a recording medium drive 23 for recording data to external output media such as FD, and a memory 11 as a storage device (storage unit) are connected via the interface 19 to the functional units including the computer (control device) 18. The memory 11 is the storage device such as a hard disk, which stores not only analysis results but also such information as the passwords each set for each operator, screen display levels, analytical parameters, requested analysis items, and results of calibration.

Figure 4:
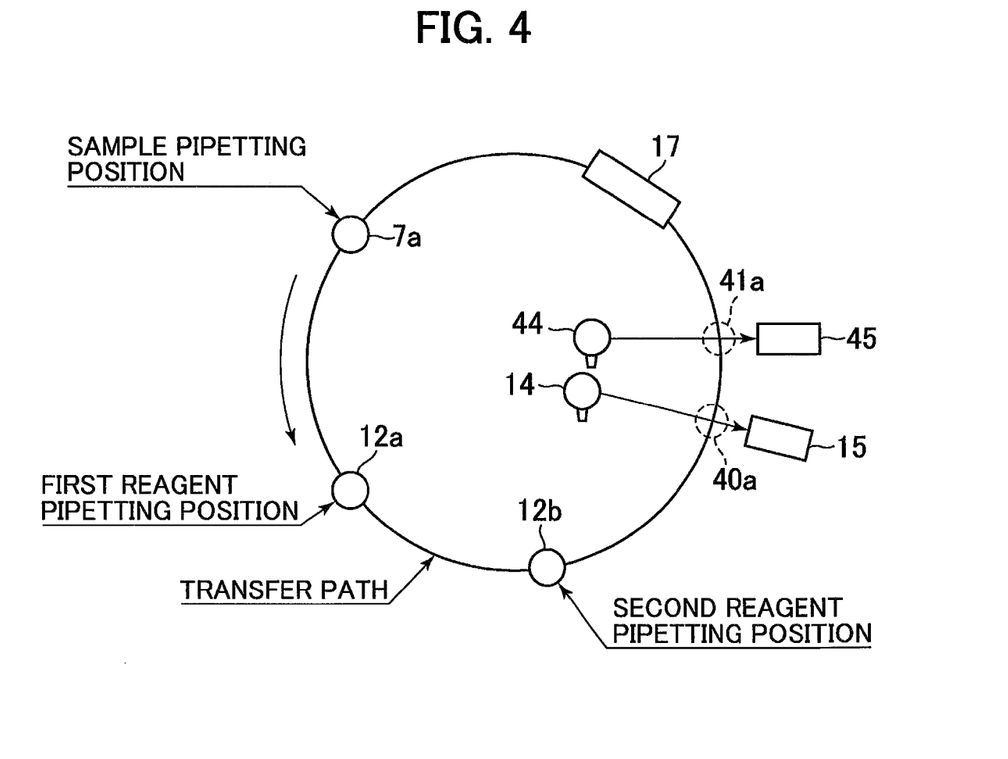
FIG. 4 is a schematic diagram showing the layout of arrangements along a transfer path of reaction cells placed on a reaction disk.

FIG. 4 is a schematic diagram showing the layout of arrangements along the transfer path of the reaction cells 2 placed on the reaction disk 1.

As shown in FIG. 4, on the transfer path of this embodiment, there are provided the sample pipetting position 7a, the first reagent pipetting position 12a, the second reagent pipetting position 12b, a scattered light detection position 40a, a transmitted light detection position 41a, and a washing position 17a, arranged counterclockwise in that order. In the respective positions, work is performed on the reaction cells 2 being transferred along the transfer path.

What follows is an explanation of the measurement principle of this embodiment regarding the measurement target sample.

(1) Measuring Method (1-1) Measurement by Use of the Absorption Photometer 41

The multi-wavelength light source (transmitted light detecting light source) 44 emits light to the liquid mixture (reaction mixture) composed of the measurement target sample and reagents. The transmitted light detector 45 measures the intensity of transmitted light having passed through the liquid mixture so that the sample is tested on the basis of measured absorbance values.

The light (ranging in wavelength from the ultraviolet light region to near-infrared light) from the multi-wavelength light source (transmitted light detecting light source) 44 is emitted to the liquid mixture (reaction mixture) composed of the sample and reagents. The transmitted light emanating from the liquid mixture is dispersed so that absorbance is calculated for a single or multiple wavelengths. And the volume of the target ingredient is quantified from the relation between the absorbance and the concentration of the reaction mixture in accordance with the Lambert-Beer law. For example, chronological changes in absorbance may be measured at predetermined intervals for about 10 minutes after a reagent is added to the sample.

Pigments in water solution generate little scattering; almost all light is absorbed. That is, only absorbance becomes larger. Because pigments have different absorption characteristics on different wavelengths, absorbance varies with the wavelength. In biochemistry, the sample is measured for a number of items such as enzymes, protein, inorganic matters, and lipids.

(1-2) Measurement by Use of the Scattered Light Photometer 40

The single-wavelength light source (scattered light detecting light source) 14 emits light to the liquid mixture (reaction mixture) composed of the measurement target sample and reagents, and the light scattered by the matters in the reaction mixture is detected by the scattered light detector 40. If the reaction mixture is water or like substance that includes no aggregates such as antigen reactants, little scattered light is generated. In this case, the scattered light grows as antigen reactants increase. And on the assumption that the definition of Rayleigh scattering addressing the scattering of light caused by particles is generally complied with, the volume of the target ingredient is quantified from the relation between the scattered light intensity and the concentration of the reaction mixture.

Where an extremely small amount of the protein ingredient in the sample is to be measured, an antibody that reacts to protein as an antigen is used as the reagent to trigger a reaction so that the concentration of the ingredient may be quantified. Because sensitivity is insufficient where only the antibody is used, latex immuno-nephelometry is adopted whereby latex particles are bound to the antibody to boost sensitivity. Particles are known to have similar absorption and scattering characteristics with regard to any wavelength. The larger the latex particle diameter, the higher the resulting sensitivity becomes. However, the larger the particle diameter, the more likely it is for the particles to precipitate in a solution when left still. This will make it difficult to perform stable measurement. Such a bound substance from the antigen-antibody reaction may or may not offer sufficient sensitivity with the absorptiometric method. For that reason, the scattered light photometer 40 is used for measurement. That is, in the measurement where latex particles or like substances are used, sensitivity is better if the scattered light photometer 40 is used to measure scattered light than if the absorption photometer 41 is adopted to make use of transmitted light.

(2) Reaction Principles

There are two major reaction principles in effect when reagents are added to the sample regarding diverse test items; one reaction principle involves using enzyme reaction, and the other reaction principle involves resorting to antigen-antibody reaction.

(2-1) Measurement by Use of Enzyme Reaction

Where the sample to be measured is allowed to react with reagents in the liquid mixture (reaction mixture) in an enzyme reaction, two kinds of reactions are often utilized: color reaction involving a substrate and enzymes, and agglutination reaction involving an antigen and an antibody. The color reaction is used in biochemical analyses of which the test items correspond to LDH (lactase dehydrogenase), ALP (alkaline phosphatase), and AST (aspartate aminotransferase), among others. The agglutination reaction is used in agglutination reaction immunoassays of which the test items correspond to CRP (C-reactive protein), IgG (immunoglobulin G), and RF (rheumatoid factor), among others.

(2-2) Measurement by Use of Antigen-Antibody Reaction

The target substance to be measured in immunoassays that use primarily antigen-antibody reaction for measurement often has a low concentration in the blood. This requires high sensitivity. For example, suppose that a reagent in which the surfaces of latex particles are sensitized (bonded) with an antibody is used to recognize and agglutinate the detection target ingredient included in the sample. In that case, the light from the multi-wavelength light source (transmitted light detecting light source) 44 is emitted to the reaction mixture, and absorbance is determined by measuring the intensity of the light having passed through the liquid without being scattered by latex aggregates (i.e., transmitted light intensity). When the measurement target ingredient included in the sample is quantified in this manner, the sensitivity of the latex immunoagglutination method is improved. The antigen-antibody binding reaction is a reaction between the antigen and the reagent, which proceeds in a relatively slow manner. Because the reaction time is on the order of several minutes, the reaction process can be monitored by taking measurements at intervals of several seconds.

(3) Of the above-described absorption photometer 41 and scattered light photometer 40, the latter tends to offer the higher sensitivity in measurements. The two photometers provide about the same repeatability in measurements. Of the two photometers, the absorption photometer 41 tends to offer the better linearity in measurements. The photometers 40 and 41 are each variably susceptible to various interference substances; the scattered light photometer 40 is more susceptible to the effects of the particulate matter of the rheumatoid factor (RF). On the other hand, the absorption photometer 41 is more resistant to the effects of the matters dissolved in the sample such as bilirubin and hemoglobin. That is, while the scattered light photometer 40 has good sensitivity because it observes particle scattering in the reaction mixture irradiated with the light of a particular wavelength, the scattered light photometer 40 is vulnerable to the effects of the particles in the sample. The absorption photometer 41 disperses the transmitted light from the reaction mixture irradiated with the light from, say, a halogen lamp (i.e., light ranging from short to long wavelengths) so that a wavelength unaffected by bilirubin or hemoglobin may be selected, which provides an extensive range of applications.

Figure 5:
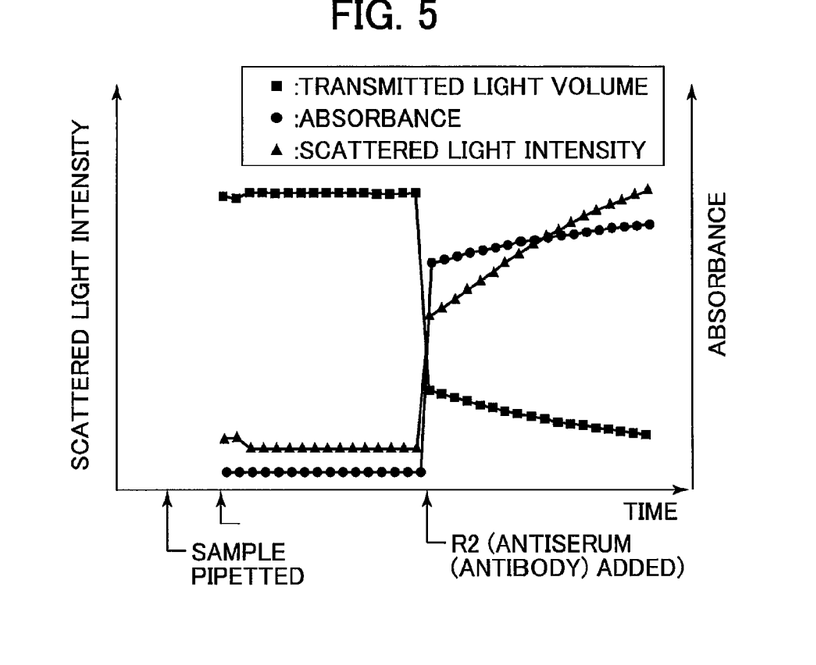
FIG. 5 is a schematic diagram showing typical changes over time in transmitted light intensity, absorbance, and scattered light intensity of a liquid mixture (reaction mixture) composed of a sample and reagents held in reaction cells.

FIG. 5 is a schematic diagram showing typical changes over time in transmitted light intensity, absorbance, and scattered light intensity of a liquid mixture (reaction mixture) composed of a sample and reagents, which is held in reaction cells. The horizontal axis represents time, and the vertical axis denotes detected amounts.

In FIG. 5, not much change is observed immediately after a first reagent (R1) is added. The detected values are found to start changing after a second reagent (R2) is added to promote the reaction. As can be seen, the intensity of transmitted light tends to become smaller and absorbance tends to become higher as the reaction progresses.

The immune reaction is also a chemical reaction in a broader sense. Chemical reactions are not limited to those taking place instantaneously when the sample and a reagent are mixed. It may take several to tens of minutes for some chemical reactions to occur. It takes several minutes for many antibody-antigen reactions to happen. Many reactions proceed rapidly during the first several minutes in particular, and slow down thereafter. In the antigen-antibody reaction, the latex antibody is used as the second reagent (R2). The most important range in which to measure the antigen-antibody reaction with the absorption photometer 41 and scattered light photometer 40 in the same cycle is after the addition of the second reagent (R2).

Coexisting materials included in the sample affect the antigen-antibody reaction during the first several minutes. With optical systems such as the absorption photometer 41 and scattered light photometer 40 of which the principles of measurement are different from one another, measurement results are differently affected even by a slight difference in time. The absorption photometer 41 measures transmitted light on one principle of measurement, whereas the scattered light photometer 41 measures scattered light on another measurement principle. The absorption photometer 41 irradiates each reaction cell with light of extensive wavelengths ranging from short to long wavelengths at once from the multi-wavelength light source 44 such as a halogen lamp, so that the transmitted light is dispersed in order to detect the intensity of the light on different wavelengths. The scattered light photometer 40 irradiates the reaction cell with the light of a single wavelength, so that the intensity of light scattered by the reaction mixture is detected. Where such multiple optical systems for capturing different characteristics of the immune reaction are used to have the measurement results evaluated comprehensively, it is preferred that the optical systems measure the reaction mixture with no difference in time therebetween. Since the exact simultaneous measurement is difficult to perform in practice, multiple photometers (scattered light photometer 40 and absorption photometer 41 in this embodiment) need to be positioned apart in such a manner that they will not interfere with each other and that the difference in time of measurement therebetween (measurement time difference) is reduced to a minimum (e.g., within one second).

One way of minimizing the measurement time difference between the absorption photometer 41 and the scattered light photometer 40 (e.g., to within several seconds) is by getting both the absorption photometer 41 and the scattered light photometer 40 to carry out their measurement within one cycle of the rotation of the reaction disk 1. Here, one cycle refers to the movement of a given reaction cell 2 starting to move from a given stop position on the transfer path until it reaches the next stop position (i.e., coming to a stop). Explained next for this embodiment are the layout of the multiple photometers 40 and 41, the sample and reagent pipetting positions with regard to the reaction cells 2, and the rotation control of the reaction disks.

Explained below is the operation of this embodiment, i.e., the control of the embodiment by the computer (control device) 18.

The analytical parameters regarding the items that can be analyzed by the automatic analyzer have been input beforehand from the keyboard 24 serving as an information input device and are stored in the memory 11. The operator selects the test items requested of each sample through the use of an operation function screen, to be discussed later.

At that point, other information such as patient ID's is also input through the keyboard 24. In order to analyze the test items designated for each sample, the sample pipetting mechanism 7 pipettes a predetermined amount of the sample from the sample container 6 into each reaction cell 2 in accordance with the analytical parameters.

The reaction cell that has received the sample is transferred by rotation of the reaction disk 1 and stops at each of the reagent pipetting positions. There, the reagent pipetting mechanisms 12A and 12B pipette predetermined amounts of reagents into the reaction cell 2 in accordance with the analytical parameters of the applicable test items. The order in which the sample and the reagents are pipetted here may alternatively be reversed, with the reagents pipetted before the sample.

Thereafter, the mixing mechanisms 33A and 33B mix the sample and the reagents. When this reaction cell 2 moves past the photometry position, the scattered light photometer 40 measures the scattered light coming from the reaction mixture. The scattered light thus measured is converted to a value proportional to the measured light intensity by the A/D converter 16. The value thus converted is admitted to the computer 18 via the interface 19. The converted value is again converted to concentration data based on the calibration curve measured beforehand by use of the analysis method predetermined for each test item. The ingredient concentration data resulting from analyzing the test items involved is output onto the printer 22 or to the screen of the CRT 25.

Before the above measuring operation is carried out, the operator sets various parameters necessary for analysis and measurement and registers samples through an operation screen. Also, the operator verifies the results of analyses after measurement on the operation screen of the CRT 25.

Explained below is the layout of the absorption photometer 41 and scattered light photometer 40 on the transfer path of the reaction disk 1, together with the rotation control of the reaction disk 1.

To suppress the measurement time difference between the absorption photometer 41 and the scattered light photometer 40 requires getting the two photometers to perform their measurement within one cycle of the rotation of the reaction disk 1. That is, in order to minimize the measurement time difference between the multiple photometers (i.e., absorption photometer 41 and scattered light photometer 40), it is necessary to perform control so that each reaction cell will move past the measurement positions of the multiple photometers within one cycle.

The reaction disk 1 is designed to have the reaction cells washed after analysis for reuse. After washing, the reaction cells again return to the sample pipetting position. The time it takes for each reaction cell 2 to start moving from the initial position (sample pipetting position) and return to the same position (called time T1 hereunder) is determined by "reaction time TR+reaction cell washing time+sample and reagent pipetting times." If it is assumed that T0 stands for the time required for each cycle, N for the number of reaction cells set on the reaction disk 1, and M for the number of reaction cells moving per cycle, then the conditions under which the multiple photometers (i.e., absorption photometer 41 and scattered light photometer 40) can perform their measurement in the same cycle are as follows:

(4) When N≤M, the measurement conditions are met unconditionally.

The layout of the reagent pipetting mechanisms 12A and 12B and the sample pipetting mechanism 7 is subject to constraints so as to accommodate the control of the reaction disk 1.

Figure 6:
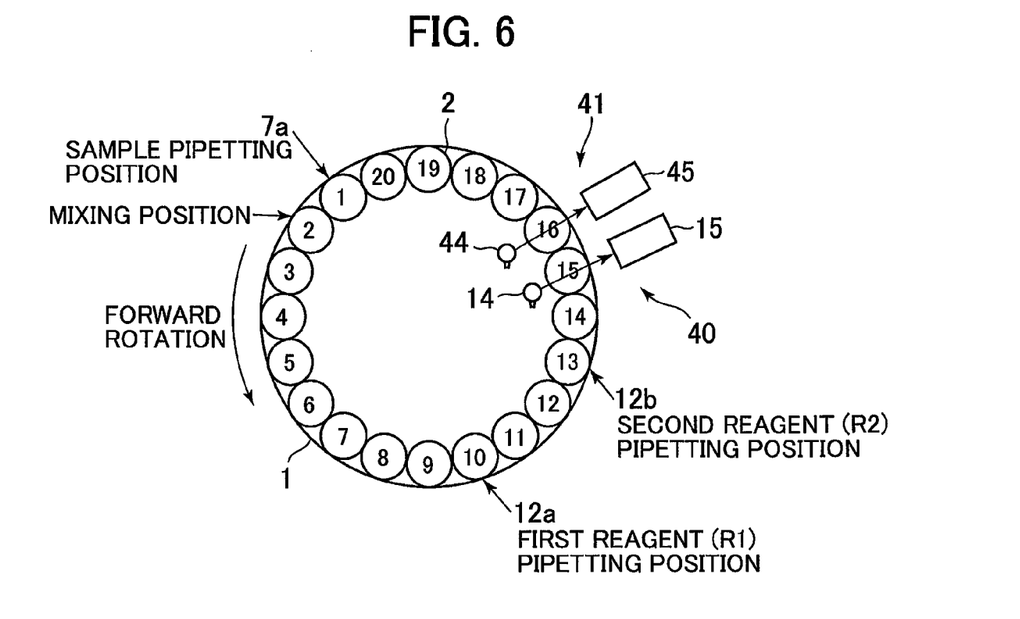
FIG. 6 is a diagram showing the operation of the reaction disk in effect when N≤M, with a measurement target reaction cell at a sample pipetting position.
Figure 7:
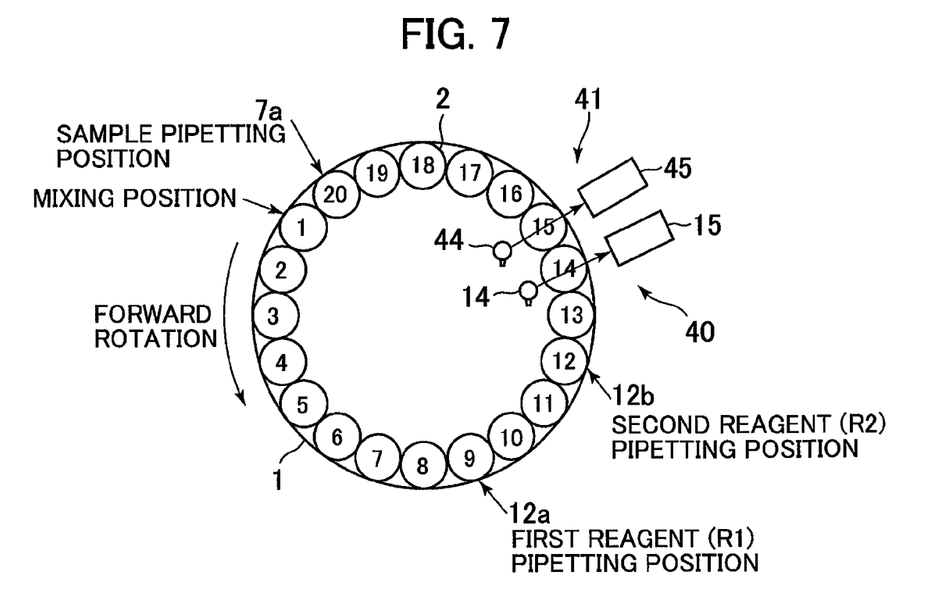
FIG. 7 is a diagram showing the operation of the reaction disk in effect when N≤M, one cycle later.

FIGS. 6 and 7 are diagrams showing the operations of the reaction disk in effect when N≤M. FIG. 6 shows the case where the reaction cell targeted for measurement is at the sample pipetting position 7a, and FIG. 7 indicates the case in effect one cycle later.

Under control of the computer (control device) 18, the reaction disk 1 is rotated one revolution plus at least one reaction cell portion (i.e., at least 360 degrees). In the examples of FIGS. 6 and 7, the reaction disk 1 is shown rotated one revolution plus one reaction cell portion. That is, in these examples, the reaction cells 2 are rotated counter-clockwise (called the forward direction hereunder) one reaction cell at a time per cycle. During this time, the reaction cells 2 move past the multiple photometers (absorption photometer 41 and scattered light photometer 40) along the transfer path on the reaction disk 1. In the same cycle, the reaction mixture in the same reaction cell 2 is measured by the multiple photometers (absorption photometer 41 and scattered light photometer 40) and measurement results are obtained thereby.

Figure 8:
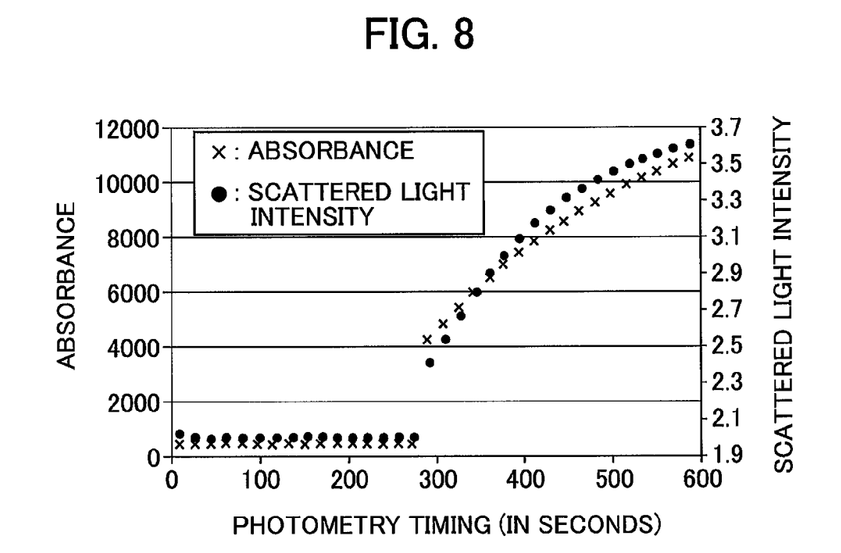
FIG. 8 shows measurement results of CRP obtained by the absorption photometer and scattered light photometer.
Figure 9:
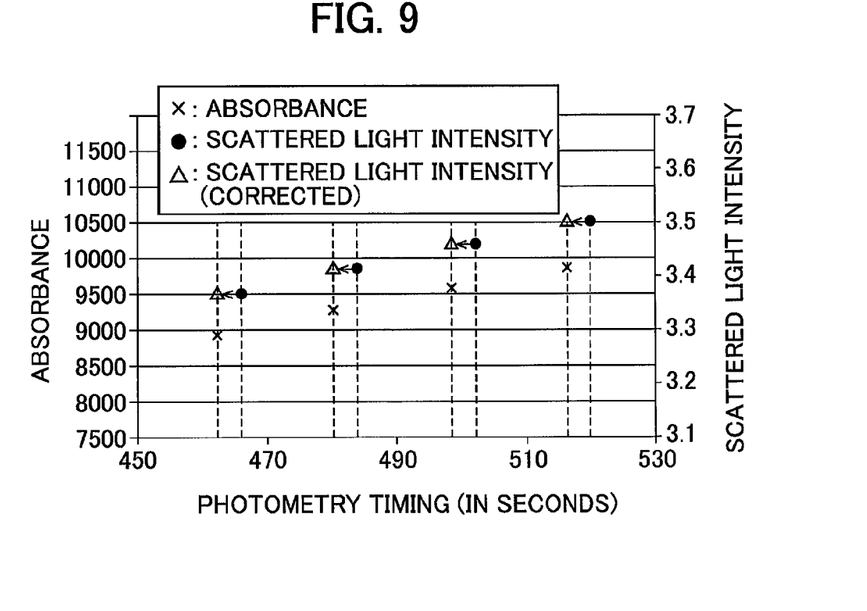
FIG. 9 is a diagram showing measurement results following time correction processing by a computer (control device).

FIG. 8 shows measurement results of CRP obtained by the absorption photometer and scattered light photometer. FIG. 9 is a diagram showing measurement results following time correction processing by the computer (control device). In FIG. 9, the measurement results given in FIG. 8 are shown only in part for purpose of simplification.

The time correction process on measurement data by the computer (control device) 18 permits time correction of the scattered light intensity or the absorption measured by the scattered light photometer 40 or by the absorption photometer 41 in reference to the times recorded in the memory 11 in association with the measurement results. When measurements are taken with the absorption photometer 41 and scattered light photometer 40 in the same cycle, a measurement time difference therebetween is bound to occur because these photometers are physically in different locations. The time correction process involves correcting the measurement time difference based on the times at which the measurements were taken. If a measurement result taken with the scattered light photometer 40 is to be corrected on the basis of the time at which the absorption photometer 41 performed the measurement, two measurement results of the scattered light photometer are used: one measurement result acquired by the scattered light photometer 40 before the time at which the absorption photometer 41 performed the measurement in a given cycle, and the other measurement result acquired by the scattered light photometer 40 after the time at which the absorption photometer 41 performed the measurement in the same cycle (i.e., two measurement results by the scattered light photometer 40 before and after the measurement result of the absorption photometer 41). In that case, the two measurement results of the scattered light photometer 40 are proportionally distributed according to the time difference between the photometers so as to calculate the measurement value of the scattered light photometer 40 corresponding to the time at which the absorption photometer 41 performed the measurement.

Given below are typical calculations of the time correction process on measurement results.

It is assumed here that AbsX stands for the X-th measurement result of absorbance and tX for the measurement time of the X-th measurement result and that IX and IY denote the scattered light intensities before and after the measurement time tX, respectively, of the measurement result AbsX on the time axis. On that assumption, the scattered light intensity corresponding to the measurement time of AbsX is given by use of the following expression:

$$IX'=(IX+IY)*(tX-tiY)/(tiX-tiY)$$

In accordance with the above expression, the data representative of all measurement points involved are converted relative to the measurement time of a given optical system. This allows the measurement data of multiple optical systems to be arranged chronologically in the same time period. There no longer exist time differences between the measurement data (see FIG. 9).

One of the following two methods is used to perform the time correction process on measurement results:

One method involves recording the actual measurement times of the different optical systems and carrying out the correction based on the measurement time differences between the measurement systems. Another method involves causing each measurement system to perform the correction at predetermined times with the reaction disk being suitably controlled.

The correction method that uses actual measurement times provides accurately corrected values. The method of making the correction by use of predetermined time differences has no need for storing the times at different measurement points; a predetermined table is used to accommodate the time differences. The latter method offers the advantages of requiring only a small storage area, having no need for a time period in which to calculate time differences, and simplifying calculation processes.

Of the two time correction methods, one that uses actual times is preferred if the measurement target reacts quickly. Where the measurement target reacts slowly, the effects are considered to be limited if predetermined correction times are used for the calculation.

(5) When $N \leq M$, the measurement conditions are subject to the following constraints:

It is necessary to control two revolutions of the reaction disk and to restrict the layout of the multiple optical systems (absorption photometer 41 and scattered light photometer 40), of the sample pipetting position, and of the reagent pipetting positions.

(5-1) When the Movement Rotation Angle of the Reaction Disk 2. Per Cycle is Between 180 and 360 Degrees The time required from the pipetting of the second reagent (R2) to the end of the reaction is about half the reaction time. If the rotation is equal to or greater than 180 degrees, it is possible to fully cover the measurement cycle from the pipetting of the second reagent up to the end of the reaction. During that time, the target reaction cell 2 is controlled to remain unstopped. That is, it is necessary to avoid selecting the conditions requiring that the reaction cell of interest move past a given photometer but stop short of another photometer.

The multiple optical systems are to be laid out within the rotation angle per cycle (360 degrees*M/N). That is, the optical systems are positioned within a predetermined angle along the rotating circumference of the reaction disk. If the operation of one cycle is one revolution (360 degrees) minus one reaction cell portion, the stop position of each reaction cell shifts one reaction cell portion short of the initial sampling position in the rotation direction per cycle. The same reaction cell 2 is allowed to move past multiple photometers within one cycle.

Figure 10:
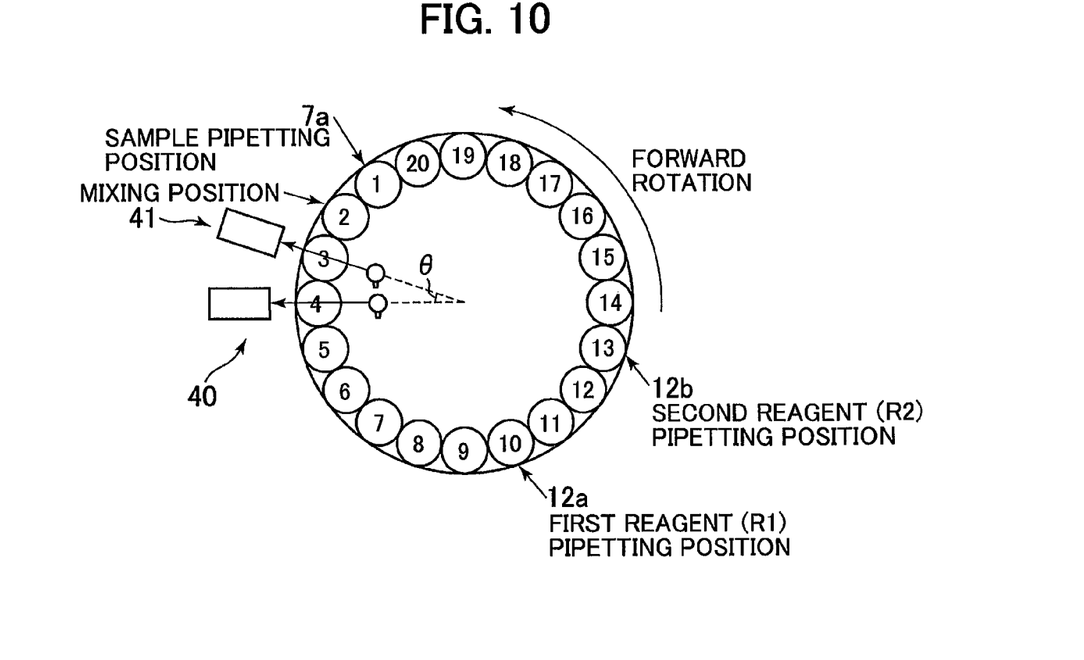
FIG. 10 is a diagram showing the operation of the reaction disk in effect when its movement rotation angle is 180 degrees or less, with the measurement target reaction cell at the sample pipetting position.
Figure 11:
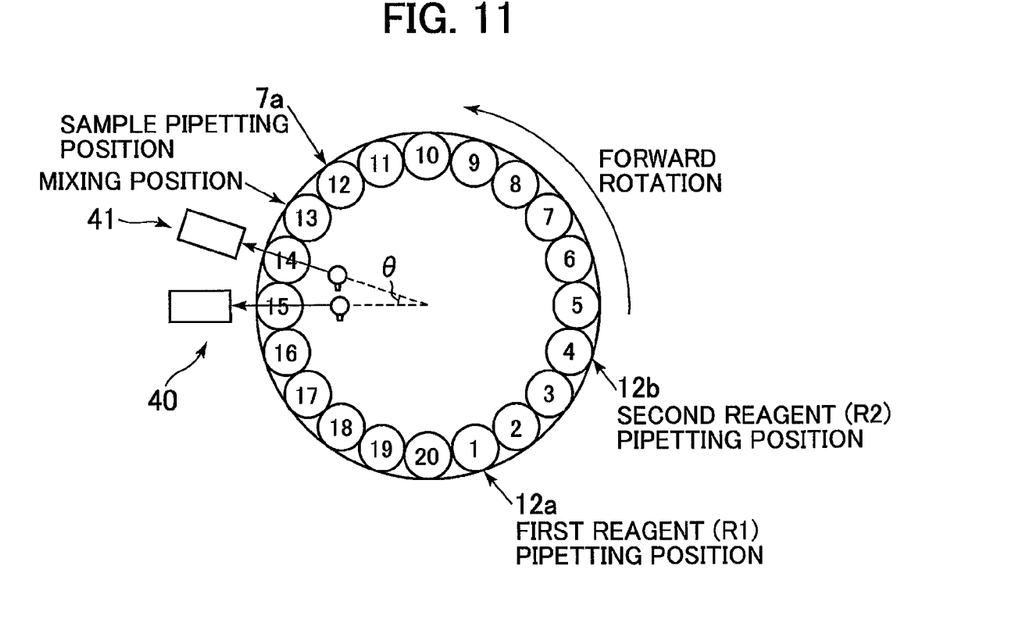
FIG. 11 is a diagram showing the operation of the reaction disk in effect when its movement rotation angle is 180 degrees or less, with the measurement target reaction cell at a first reagent pipetting position one cycle later.
Figure 12:
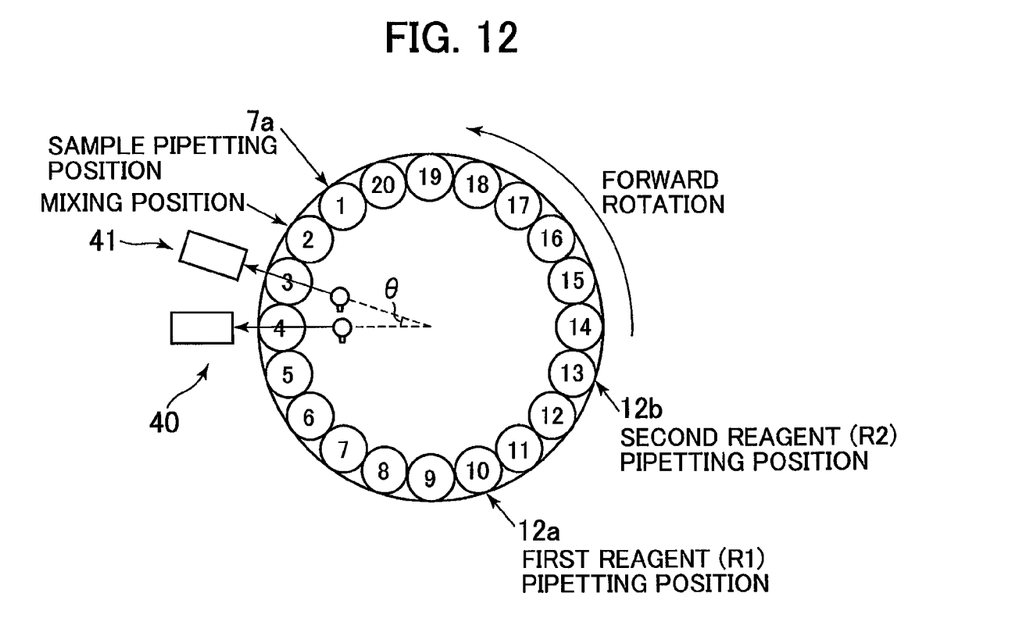
FIG. 12 is a diagram showing the operation of the reaction disk in effect when its movement rotation angle is 180 degrees or less, with the measurement target reaction cell moving past a second reagent pipetting position towards a mixing position.

(5-2) When the Movement Rotation Angle of the Reaction Disk 2 is 180 Degrees or Less Per Cycle FIGS. 10 through 12 are diagrams showing the operations of the reaction disk in effect when the movement rotation angle is 180 degrees or less. FIG. 10 shows the case in which the measurement target reaction cell is at the sample pipetting position. FIG. 11 indicates the case in which the measurement target reaction cell is at the first reagent pipetting position one cycle later. FIG. 12 depicts the case where the measurement target reaction cell has moved from the position shown in FIG. 11 past the second reagent pipetting position towards the mixing position.

Since the time required from the pipetting of the second reagent (R2) to the end of the reaction is about half the reaction time, if the rotation is 180 degrees or less, it is impossible to perform control so that a given reaction cell will move past the multiple photometers (absorption photometer 41 and scattered light photometer 40) in the measurement cycle ranging from the pipetting of the second reagent to the end of the reaction. In the antigen-antibody reaction, the measurements taken in several cycles after the addition of the second reagent are important in securing the sensitivity of the reagents. The reaction cell 2 of interest is controlled to remain unstopped after the addition of the second reagent.

The angle θ at which the multiple optical systems (absorption photometer 41 and scattered light photometer 40) are positioned to one another is the rotation angle per cycle or less (360 degrees*M/N). That is, the optical systems are located within the rotation angle of one cycle centering on the reaction disk 2 over the transfer path of the reaction disk 1. In the first measurement cycle following the addition of the second reagent, the multiple optical systems (absorption photometer 41 and scattered light photometer 40) are to be arranged so that they can perform their measurement without fail. The reaction cell 2 is stopped short of the multiple photometers (absorption photometer 41 and scattered light photometer 40) in the rotation direction (forward direction) of the reaction disk 1. In the first measurement cycle following the start of the rotation of the reaction disk 1, the two photometers (absorption photometer 41 and scattered light photometer 40) are to be arranged so that they can perform their measurement.

(5-3) When the Movement Rotation Angle of the Reaction Disk 2 is 90 Degrees or Less Per Cycle Suppose that the movement angle is as small as 90 degrees or less, that the reaction time is 10 minutes following the sampling and that 5 minutes have elapsed since the addition of the second reagent. In that case, the reaction time in which the multiple photometers are moved past within the same cycle lasts about 2 or 3 minutes, which fails to cover the entire reaction time. It is preferred that the angle at which the reaction cell is moved per cycle be about 180 degrees. In this case, the reaction time of approximately 5 minutes can be covered.

(5-4) Typical Measurement Results Controlled Under the Condition of N≥M

Figure 13:
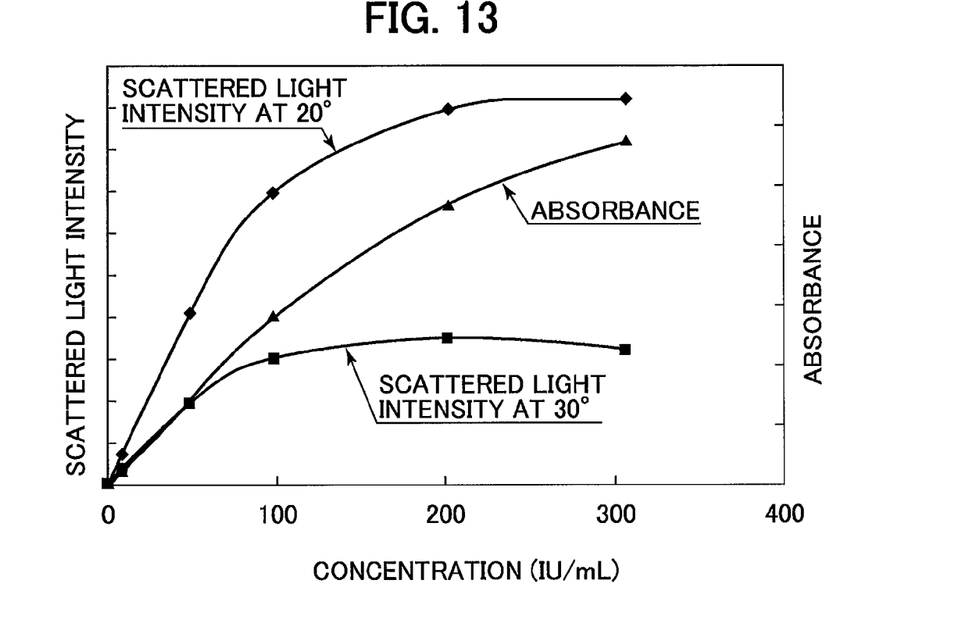
FIG. 13 is a diagram showing scattered light intensity obtained by the scattered light photometer with a measuring reagent RF and a tumor marker AF in use.
Figure 14:
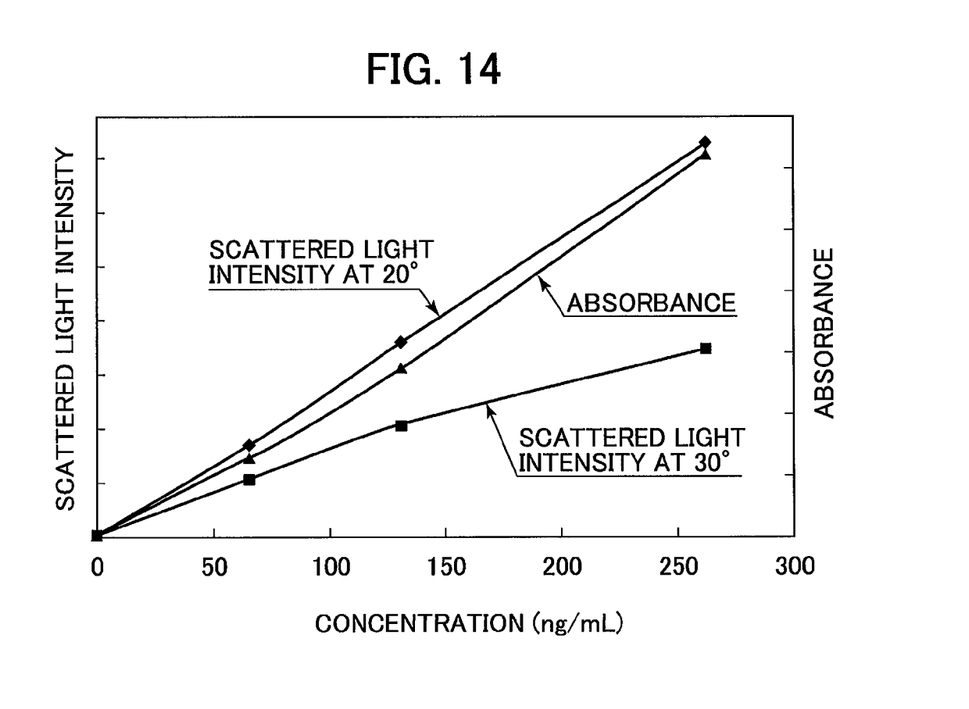
FIG. 14 is a diagram showing measurement results of linearity obtained by the absorption photometer.

The number (N) of reaction cells is 160, and the number (M) of moved reaction cells per cycle is 150. The second reagent is added 5 minutes after the first reagent was added. Following the addition of the second reagent, the absorption photometer 41 and scattered light photometer 40 perform the measurement within the same cycle. FIG. 13 shows the scattered light intensity obtained by the scattered light photometer 40 with a measuring reagent RF and a tumor marker AF in use. FIG. 14 shows measurement results of linearity obtained by the absorption photometer. FIG. 13 shows two cases of measurement: one in which the detector of the scattered light photometer 40 is positioned at 20 degrees relative to the optical axis, and another in which the detector is positioned at 30 degrees in like conditions.

(6) Conversion to Concentration

Figure 15:
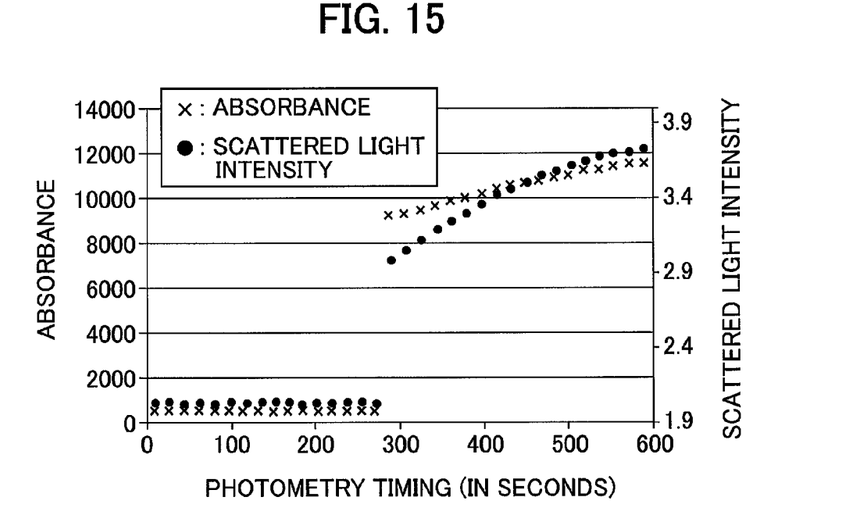
FIG. 15 is a diagram showing typical measurement results of insulin.

Prior to the start of measurement, the automatic analyzer of this embodiment performs calibration including the calculation of a calibration curve using a standard solution with the multiple optical systems (scattered light photometer 40 and absorption photometer 41). The calibration curve is created on the basis of the measurement results from the time correction process carried out on the measurement results of the standard solution. In the subsequent measurement of general samples (target measurement sample), measurement results are obtained on the basis of the measurement results and calibration curve, which have been undergone the time correction process. Each of the multiple optical systems (scattered light photometer 40 and absorption photometer 41) performs the calibration individually. It follows that when a given optical system has completed the conversion of patient specimens to concentration values following calibration, the processing by that system is terminated without discrepancies in measurements being generated. However, if the measurement results of the multiple optical systems (scattered light photometer 40 and absorption photometer 41) are to be compared, the comparison is not simple because there may be discrepancies in measurements between the scattered light photometer 40 performing the measurement at a given time and the absorption photometer 41 carrying out the measurement at a different time. Where chemical reactions are dealt with, the effects of measurement time differences on measurement results can become significant. FIG. 15 shows typical measurement results of insulin. The reactions of CRP over time shown in FIG. 8 differ from one test item to another. Where the same reaction is measured by optical systems whose measurement principles differ, such as by the scattered light photometer 40 and absorption photometer 41, the time correction process can be seen to be critical.

The effects offered by the embodiment structured as described above are explained below.

With automatic analyzers of the existing technology, the measurement target sample is measured for absorbance or for scattered light in analyzing the sample (biological sample such as blood or urine) qualitatively and quantitatively. In the measurement of absorbance, the light ranging from short to long wavelengths is emitted to the sample and the transmitted light emanating therefrom is dispersed. This provides the advantage of ensuring a wide range of applications because a wavelength unaffected by bilirubin or hemoglobin can be selected, for example. In the measurement of scattered light, there is the advantage that sensitivity is high because the reaction solution is irradiated with the light of a specific wavelength for observation of particle scattering. However, it is necessary to consider the fact that the measurement is vulnerable to the effects of particles in the sample. Conceivably, measurement accuracy could be improved by performing both the measurement of scattered light and the measurement of absorbance on the same measurement target sample. However, since the measurement of scattered light and that of absorbance are aimed at the measurement target sample of which the state varies over time starting from the addition of a predetermined reagent, there is fear that the time difference between scattered light measurement and absorbance measurement may affect the measurement results.

By contrast, this embodiment includes the sample pipetting mechanism, reagent pipetting mechanisms, mixing mechanisms, scattered light photometer, and absorption photometer located on the transfer path of reaction cells that are transferred in the circumferential direction by rotation of the reaction disk. Scattered light intensity and absorbance are arranged to be measured by causing the reaction cells to move past both the scattered light detection position and the transmitted light detection position in the same process of movement. This makes it possible to suppress the effects on measurement results of the difference in time between scattered light measurement and absorbance measurement, thereby improving measurement accuracy.

DESCRIPTION OF REFERENCE CHARACTERS

1 Reaction disk
2 Reaction cell
3 Reaction vessel
4 Reaction vessel water circulation device
5 Sample disk
7 Sample pipetting mechanism
9A, 9B Reagent cooling box
10A, 10B Reagent bottle
11 Memory
12A, 12B Reagent pipetting mechanism 13A First reagent disk
13B Second reagent disk
14 Single-wavelength light source (scattered light detecting light source)
15 Scattered light detector
16 A/D converter
17 Washing mechanism
18 Computer (control unit)
19 Interface
20 Sample pipetting control unit
21 Reagent pipetting control unit
22 Printer
23 Recording medium drive
24 Keyboard
25 CRT display unit
33A, 33B Mixing mechanism
34A, 34B Reading device
40 Scattered light photometer
41 Absorption photometer
44 Multi-wavelength light source (transmitted light detecting light source)
45 Transmitted light detector

The invention claimed is:

1. An automatic analyzer comprising:
a plurality of reaction cells that hold a liquid mixture of a sample and a reagent;
a disk-shaped reaction disk that has the reaction cells arranged thereon circumferentially and rotates to transfer the reaction cells on a transfer path in a circumferential direction of the reaction disk;
a sample pipetting mechanism located on the transfer path, the sample pipetting mechanism pipetting the sample from a sample container holding the sample into the reaction cells;
a reagent pipetting mechanism located on the transfer path, the reagent pipetting mechanism pipetting the reagent from a reagent container holding the reagent into the reaction cells;
a mixing mechanism located on the transfer path that mixes the liquid mixture held in the reaction cells;
at least one scattered light photometer that has a scattered light detecting light source for emitting scattered light detecting light to the liquid mixture in the reaction cells moving past a predetermined scattered light detection position on the transfer path, the scattered light photometer further having a scattered light detector for detecting scattered light emanating from the liquid mixture corresponding to the light emitted from the scattered light detecting light source, the scattered light photometer further measuring scattered light intensity from the liquid mixture;
at least one absorption photometer that has a transmitted light detecting light source for emitting transmitted light detecting light to the liquid mixture in the reaction cells moving past a predetermined transmitted light detection position different from the scattered light detection position on the transfer path, the absorption photometer further having a transmitted light detector for detecting transmitted light having passed through the liquid mixture corresponding to the light emitted from the transmitted light detecting light source, the absorption photometer further measuring absorbance of the liquid mixture;
a control device that programmed to control the reaction disk, the sample pipetting mechanism, the reagent pipetting mechanism, the mixing mechanism, the at least one scattered light photometer, and the at least one absorption photometer so that the scattered light intensity and the absorbance are measured by controlling the reaction cells to move past the scattered light detection position and the transmitted light detection position in a same process of movement which is at least one revolution of the reaction disk;
a storage unit that stores measurement values of the scattered light intensity measured by the at least one scattered light photometer and measurement times at which the measurement values of the scattered light intensity were obtained, the storage unit further storing measurement values of the absorbance measured by the at least one absorption photometer and the measurement times at which the measurement values of the absorbance were obtained,
wherein the control device is further programmed to consider one of the measurement times stored in the storage unit to be a reference time, and correct one of the measurement values of one of the measurement times closest to the reference time of the measurement results of the scattered light intensity measured before the reference time,
wherein the control device is further programmed to correct the one of the measurement values of the scattered light intensity at tiX which is the one of the measurement times closest to the reference time of the measurement results of the scattered light intensity measured before the reference time based on the following expression:

$$IX'=(IX+IY)*(tX-tiY)/(tiX-tiY),$$

wherein tX denotes the reference time which is one of the measurement times of an X-th one of the measurement results of the absorbance, IX and IY denote the measurement results of the scattered light intensity before and after the reference time, respectively, tiX and tiY denote the measurement times of the measurement results of IX and IY of the scattered light intensity, respectively, and IX' denotes the one of the measurement values of the scattered light intensity at the measurement time tiX.

2. The automatic analyzer according to claim 1, wherein the process of movement is longer than the transfer path corresponding to one revolution of the reaction disk.

3. The automatic analyzer according to claim 1, wherein a maximum value of the difference between the measurement times obtained by the at least one scattered light photometer and by the at least one absorption photometer in the same process of movement is one second or less.

4. The automatic analyzer according to claim 1, wherein the control device causes a pipetting process to be implemented followed by a measurement process, the pipetting process being one in which the reagent for triggering an observation target reaction in the liquid mixture is pipetted by the reagent pipetting mechanism into the reaction cells, the measurement process being one in which the scattered light photometer and the absorption photometer perform the measurement.

5. An automatic analyzer comprising:
a plurality of reaction cells that hold a liquid mixture of a sample and a reagent;
a disk-shaped reaction disk that has the reaction cells arranged thereon circumferentially and rotates to transfer the reaction cells on a transfer path in a circumferential direction of the reaction disk;

at least one sample pipetting mechanism located on the transfer path, the at least one sample pipetting mechanism pipetting the sample from a sample container holding the sample into the reaction cells;

a reagent pipetting mechanism located on the transfer path, the reagent pipetting mechanism pipetting the reagent from a reagent container holding the reagent into the reaction cells;

a mixing mechanism located on the transfer path that mixes the liquid mixture held in the reaction cells;

at least one scattered light photometer that has a scattered light detecting light source for emitting scattered light detecting light to the liquid mixture in the reaction cells moving past a predetermined scattered light detection position on the transfer path, the scattered light photometer further having a scattered light detector for detecting scattered light emanating from the liquid mixture corresponding to the light emitted from the scattered light detecting light source, the scattered light photometer further measuring scattered light intensity from the liquid mixture;

at least one absorption photometer that has a transmitted light detecting light source for emitting transmitted light detecting light to the liquid mixture in the reaction cells moving past a predetermined transmitted light detection position different from the scattered light detection position, the absorption photometer further having a transmitted light detector for detecting transmitted light having passed through the liquid mixture corresponding to the light emitted from the transmitted light detecting light source, the absorption photometer further measuring absorbance of the liquid mixture;

a control device programmed to control the reaction disk in such a manner that the reaction cells move past the transmitted light detection position in a same process of movement as that in which the reaction cells move past the scattered light detection position, and the same process of movement is at least one revolution of the reaction disk;

a storage unit that stores measurement values of the scattered light intensity measured by the at least one scattered light photometer and measurement times at which the measurement values of the scattered light intensity were obtained, the storage unit further storing measurement values of the absorbance measured by the at least one absorption photometer and the measurement times at which the measurement values of the absorbance were obtained, wherein the control device is further programmed to consider one of the measurement times stored in the storage unit to be a reference time, and correct one of the measurement values of one of the measurement times closest to the reference time of the measurement results of the scattered light intensity measured before the reference time, wherein the control device is further programmed to correct the one of the measurement values of the scattered light intensity at tiX which is the one of the measurement times closest to the reference time of the measurement results of the scattered light intensity measured before the reference time based on the following expression:

$IX'=(IX+IY)*(tX-tiY)/(tiX-tiY)$ wherein tX denotes the reference time which is one of the measurement times of an X-th one of the measurement results of the absorbance, IX and IY denote the measurement results of the scattered light intensity before and after the reference time, respectively, tiX and tiY denote the measurement times of the measurement results of IX and IY of the scattered light intensity, respectively, and IX' denotes the one of the measurement values of the scattered light intensity at the measurement time tiX.

* * * * *